United States Patent [19]

Holme

[11] Patent Number: 4,695,460

[45] Date of Patent: Sep. 22, 1987

[54] SYNTHETIC, PLASMA-FREE, TRANSFUSIBLE PLATELET STORAGE MEDIUM

[75] Inventor: Stein Holme, Virginia Beach, Va.

[73] Assignee: American Red Cross, Washington, D.C.

[21] Appl. No.: 841,435

[22] Filed: Mar. 19, 1986

[51] Int. Cl.$^4$ .......................... A61K 35/14; A01N 1/02
[52] U.S. Cl. .................................... 424/101; 424/127; 424/153; 435/2; 435/240.31
[58] Field of Search ...................... 424/101, 127, 153; 435/2, 240, 241

[56] References Cited

U.S. PATENT DOCUMENTS

| | | |
|---|---|---|
| 2,786,014 | 3/1957 | Tullis . |
| 3,629,071 | 12/1971 | Sekhar . |
| 4,390,619 | 6/1983 | Harmening-Pittiglio . |
| 4,447,415 | 5/1984 | Rock et al. . |

OTHER PUBLICATIONS

9–Biochem, Methods, vol. 91, 1979, 91:136650y.
Chemical Abstracts, vol. 77, 1972, 73201r.
Remington's Pharmaceutical Sciences, Mack Publishing Co., 14th Edition (1970), pp. 815 to 847.
Hematology, Williams et al., Second Edition, McGraw-Hill Book Co., (1977), pp. 1553–1561.
Baldini et al., Blood, 15:909 (1960) and Bagdasarov et al., Blood, 16:1667 (1960).
Abstract by Adams et al., "Abstracts of the 18th Congress of the International Society of Blood Transfusion Munchen", Jul. 1984, p. 124.
Pages from article Tullis et al., "Preserved Platelets: Their Preparation Storage and Clinical Use, from the Dept. of Medicine and Biological Chemistry, Harvard Medical School (1958).
PCT application WO 85/02116 to Murphy.
Baldini et al., *Blood,* 16:1669 (1960), pp. 1669–1692.

*Primary Examiner*—Sam Rosen
*Attorney, Agent, or Firm*—Fisher, Christen & Sabol

[57] ABSTRACT

The invention is a sterile, plasma-free platelet storage medium. The platelet storage medium includes a physiologically compatible, aqueous electrolyte solution. In one liter of this electrolyte solution there is between about 3.0 grams and about 7.5 grams of dextrose, between about 3.0 grams and about 6.0 grams of sodium citrate, and between about 2.0 grams and about 4.2 grams of sodium bicarbonate. The platelet storage medium is isotonic and has a pH in a range of between about 6.8 and about 7.4. The platelet storage medium is capable of storing and preserving platelets for at least 10 days.

20 Claims, No Drawings

SYNTHETIC, PLASMA-FREE, TRANSFUSIBLE PLATELET STORAGE MEDIUM

BACKGROUND OF THE INVENTION

1. Technical Field

The present invention is related to a synthetic blood platelet suspension medium. More particularly, the present invention is related to a synthetic preservation medium for platelets which (1) is free of blood plasma and proteins, (2) extends platelet shelf life and improves the quality of platelet concentrates stored for transfusion and (3) is free of organic compounds other than dextrose and citrate.

2. State of the Art

Blood is composed of two major portions. These portions can be recognized when a specimen of blood is taken and clotting is prevented. That portion of the blood which settles to the bottom of the vessel holding the specimen is termed the "formed elements". The formed elements comprise red blood cells and other particulate components such as white blood cells and platelets which are also known as thrombocytes. The formed elements are characteristically 40 to 50 percent of the bulk of normal human blood. The cloudy liquid which does not settle in a blood specimen is the portion of the blood known as plasma. Plasma is primarily water, but contains inorganic and organic substances as well as dissolved gases and miscellaneous foreign substances. The inorganic substances contained in blood plasma are primarily electrolytes. The most significant of these electrolytes are presented in Table 1.

TABLE 1

| | |
|---|---|
| Sodium | 142.0 mEq/l |
| Potassium | 4.3 mEq/l |
| Calcium | 5.0 mEq/l |
| Magnesium | 3.4 mEq/l |
| Chloride | 104.0 mEq/l |
| Bicarbonate | 27.0 mEq/l |
| Phosphate | 2.3 mEq/l |
| Sulfate | 0.6 mEq/l |

The most significant organic substances found in the plasma are lactic acid, urea, amino acids, creatinine, glucose, hormones, proteins, albumins, and globulins.

Modern medicine has been developing solutions that are added to blood in vivo and/or mixed with blood in vitro. Products that are used for adding to blood in vivo are primarily used for intravenous feeding, pharmaceutical vehicles, and/or electrolyte replacement in patients who are bedfast. These solutions are primarily comprised of water that contains dextrose and, optionally, electrolytes. Dextrose is typically present in these solutions in about a 5 percent concentration and provides a nutrient for blood cells or tissue cells. The electrolytes contained in these solutions vary widely. The solutions that contain electrolytes that most closely resemble blood plasma contain a plurality of the electrolytes presented in Table 1. A specific example of a dextrose and electrolyte solution suitable for in vivo addition in blood is Locke-Ringer's solution. The formula for Locke-Ringer's solution is presented in Table 2.

TABLE 2

| | |
|---|---|
| Reagent Sodium Chloride | 9.0 Gm |
| Reagent Potassium Chloride | 0.42 Gm |
| Reagent Calcium Chloride | 0.24 Gm |
| Reagent Magnesium Chloride | 0.2 Gm |
| Sodium Bicarbonate | 0.5 Gm |

TABLE 2-continued

| | |
|---|---|
| Dextrose | 0.5 Gm |
| Water, recently distilled from a hard glass flask, in a sufficient quantity, to make | 1000 ml |

Other solutions suitable for the addition of blood in vivo can be found in Remington's Pharmaceutical Sciences, Mack Publishing Company, 14th Edition (1970), pages 815 to 847.

Solutions that are added to blood in vitro are principally concerned with preserving either whole blood or separated components of the blood such as red blood cells, white blood cells, or mixtures of various substances. When platelets are included in a component of blood that is to be collected and preserved in vitro an anticoagulant is added. The most frequently used anticoagulant added to collected whole blood is known as "acid-citrate-dextrose" or "ACD". This anticoaulant solution contains (1) citric acid and sodium citrate in concentrations sufficient to produce an optimum physiological pH and (2) dextrose in concentrations sufficient for long term preservation of red blood cells. A solution that has been found desirable to preserve both whole blood and fractions of whole blood is known as "anticoagulant citrate-phosphate-dextrose solution" or "CPD". The components of anticoagulant citrate-phosphate-dextrose solution are presented in Table 3.

TABLE 3

| | |
|---|---|
| Citric Acid (anhydrous) | 3.0 Gm |
| Sodium Citrate (dihydrate) | 26.3 Gm |
| Sodium Biphosphate (monohydrate; $NaH_2PO_4H_2O$) | 2.22 Gm |
| Dextrose | 25.5 Gm |
| Water for Injection, in a sufficient quantity to make | 1000 ml |

Specific elements of the particulate component of blood can be separated and preserved for later transfusion. Traditional processes can be used to collect and preserve white blood cells and platelets together. More modern processes allow platelets to be separated, stored, and reinfused into recipients suffering from platelet deficiency. Rapid deterioration of these elements occurs after separation and storage by these processes. It is hypothesized that deterioration in platelet quality during storage is due to the activation of plasma clotting factors released during storage.

The storage of separated platelets or "platelet concentrates" that are intended for transfusion is typically conducted by one of three processes. These processes involve platelet suspension in gelatin followed by chilling of the suspension, freezing or freezing and lyophilizing platelets, and liquid storage of platelets. These processes are generally described in *Hematology*, Williams et al., Second Edition, McGraw-Hill Book Company (1977), pages 1553-61, herein incorporated by reference.

One of the oldest techniques known for the storage of platelets is disclosed in U.S. Pat. No. 2,786,014 to Tullis. The platelets are suspended in 40 milliliters of water with between 0.3 to 1.2 grams of gelatin with sodium acetate and sodium chloride. The suspension is stored at 4° C. This process has generally been discontinued because chilling or low temperatures cause morphological changes that alter the normal discoid shape of platelets into a spherical shape. This distortion of the platelet shape at temperatures below 15° C. becomes permanent after a few hours.

The technique of platelet storage by freezing has been known for years, but has does not have wide clinical application. In this process platelets are suspended in a 5 to 10 percent glycerol or glycerol-glucose solution and frozen. The platelets can remain frozen for days or months before thawing and reinfusing. The recovery of viable platelets after freezing and thawing is only about 30 percent. This recovery of viable platelets is about one-half of that recovered by processes that separate fresh platelets and do not involve freezing. This loss of viable platelets decreases the desirability of the freezing process.

The most promising processes for platelet storage involve liquid storage of platelets in temperatures, that do not produce morphological damage to the stored platelets, such as temperatures of about 22° C. The solutions for liquid storage of platelets generally include one or more of the electrolytes listed in Table 1, dextrose or glucose, an anticoagulant, and one or more additives. These solutions typically preserve platelets for about 24 to about 72 hours. Some additives can only be used for experimental purposes because the additives fail to meet safety or regulatory requirements or, as with many organic and especially proteinaceous compounds, can sensitize the recipient and cause allergic reactions upon repeated exposure to the compounds.

Platelet concentrates for most clinical purposes are currently prepared from collected units of citrate-phosphate-dextrose anticoagulated whole blood and stored in approximately 50 to 60 milliliters of the anticoagulated plasma or "CPD-plasma". The CPD-plasma is infused together with the platelets into patients in need of platelet transfusions. In that this process requires the use of plasma for the storage of the platelets, that plasma is not available for other purposes in the treatment of patients. It is, therefore, desirable to store or suspend viable platelets in a plasma-free medium so as to not detract from the amount of collected plasma available for transfusion into patients. Additionally, the plasma used to suspend platelets can cause an allergic reaction to occur in a patient after a transfusion because of a blood type or "ABO" incompatibility between a donor and a recipient of the transfused platelets.

Other studies describing preservation media for platelets were published by Baldini et al., *Blood* 15: 909 (1960) and Bagdasarov et al., *Blood* 16: 1667 (1960). The preservation medium described by Baldini contained inosine and adenine in addition to glucose, plasma, and a phosphate buffer. Baldini et al. demonstrated that about 40% of the platelets can remain viable using radiolabeling after six days of storage at 4° C. However, the infused platlets disappeared from the circulation in the undesirably short period of time of less than 20 hours. The preservation media described by Bagdasarov et al. is a salt solution containing glucose and EDTA. The Bagdasarov et al. solution also requires storage at 4° C. The in vitro results of this disclosure had undesirably low platelet viability. Storage of the platelets at 4° C. and the use of EDTA decrease the function and viability of the platelets.

U.S. Pat. No. 3,629,071 to Sekhar discloses preservation solutions for platelets containing glucose, magnesium chloride, and prostaglandins. The suspensions of this patent preserve the hemostatic function of the platelets. This function was demonstrated by incubating rat platelet rich plasma in the presence of PGE for 48 hours at 4° C. and performing aggregation experiments. The suitability of using these solutions for storage of human platelet concentrates for transfusion and the in vivo viability of platelets stored in these solutions is not documented. The use of additives such as prostaglandins is for experimental purposes and to date is not approved by the U.S. Food and Drug Administration for use in substances for infusion into humans.

U.S. Pat. No. 4,390,619 to Harmening-Pittiglio discloses a platelet storage medium using an ion-exchange resin. The improvement presented by this invention consists of a water insoluble polymer containing releasable phosphate or bicarbonate ions. These ions supply a physiologically acceptable, sustained release of buffer in the medium. The sustained release of buffer maintains both pH and ATP levels that are equal to at least 60% of the level found in freshly prepared platelets. The medium can store platelets for a period of at least seven days at 22° C. A substantial and undesirable loss of platelets occurs with this medium during storage in the resin bags. For example, at day 7 and with 1 gram of resin the reported platelet count is, respectively, 43 percent of the initial platelet count in Fenwal bags and 61 percent of the initial platelet count in Cutter bags. There is no documentation in this patent of in vivo studies demonstrating platelet viability upon infusion.

Studies using a plasma-free medium for storage of platelet concentrates have been described in an abstract by Adams et al., "Abstracts of the 18th Congress of the International Society of Blood Transfusion Munchen", July, 1984, page 124. The composition of this medium is not disclosed, but platelets can be stored in this medium for up to five days and produce in vitro results similar to that obtained by storing platelets in plasma. No in vivo studies are reported in this document.

U.S. Pat. No. 4,447,415 to Rock et al. discloses a liquid storage medium for platelets that is plasma-free. The medium of this invention uses one or more additives in conjunction with a saline and anticoagulant, dextrose-containing solution that is desirably a form of CPD-Tyrode's solution. The additives disclosed as being suitable for use with this invention include (1) reversible inhibitors that are organic compounds such as indomethacin, quinacrine, or vitamin E and (2) substances or raise cyclic adenosine monophosphate levels such as prostaglandins $E_1$, $D_2$, or $I_2$. As stated above many of these additives fail to meet safety and regulatory requirements required for substances for infusion into humans and are, therefore, only suitable for experimental use or only for in vitro use. Other additives disclosed as suitable for use with this invention include (1) nutrients such as fructose and other sugars, adenine, or acetyl CoA and (2) buffers such as phosphate and certain amino acids. The organic compounds or additives identified as nutrients do not eliminate the requirement for the presence of dextrose in the medium and do not satisfy the nutrient requirement for the platelets for periods of storage time extending beyond about 5 days. The additives identified as buffers cannot maintain a balanced pH during extended platelet storage periods beyond about 5 days. These buffers cannot adequately buffer the amount of lactic acid produced by viable, suspended platelets as a by-product from the consumption of dextrose that occurs when the platelets are stored at temperatures of at least about 22° C.

The industry is lacking a platelet storage medium that is free of plasma and organic compounds, other than dextrose and an anticoagulant such as citric acid, and preserves platelets without chilling or in temperatures of at least about 22° C. for storage periods of more than 7 days with minimal loss of viability and without the use of additives that are either unsafe or unapproved for in vivo human use.

SUMMARY OF THE INVENTION

The invention is a sterile, plasma-free platelet storage medium. The platelet storage medium includes a physiologically compatible, aqueous electrolyte solution. In one liter of this electrolyte solution there is between about 3.0 grams and about 7.5 grams of dextrose, between about 3.0 grams and about 6.0 grams of sodium citrate, and between about 2.0 grams and about 4.2 grams of sodium bicarbonate. The platelet storage medium is isotonic and has a pH in a range of between about 6.8 and about 7.4. The platelet storage medium is capable of storing and preserving platelets for at least 14 days at a temperature of at least about 22° C.

The platelet storage medium can have electrolytes including, in 1 liter of the medium, between about 6.4 grams and about 7.6 grams of sodium chloride, between about 0.2 gram and about 0.4 gram of potassium chloride, between about 0.1 gram and about 0.4 gram of calcium chloride, between about 0.2 gram and about 0.4 gram of magnesium sulphate, and between about 0.1 gram and about 0.6 gram of monobasic sodium phosphate.

The invention also includes a process for preserving platelets in a sterile, plasma-free platelet storage medium.

DETAILED DESCRIPTION OF THE INVENTION

This invention is a sterile, plasma-free platelet storage medium. The platelet storage medium includes a physiologically compatible, aqueous electrolyte solution. In one liter of this electrolyte solution there is between about 3.0 grams and about 7.5 grams of dextrose, between about 3.0 grams and about 6.0 grams of sodium citrate, and between about 2.0 grams and about 4.2 grams of sodium bicarbonate. The platelet storage medium is isotonic and has a pH in a range of between about 6.8 and about 7.4. Except for dextrose and citric acid or citric acid derivatives, the most desirable platelet storage mediums of this invention are free of organic compound additives. The term "viable" platelets as used herein means that substantial concentrations of the isolated platelets suspended in the platelet storage medium retain their normal and inherent physiological, functional, and structural properties such that the stored platelets are capable of being infused and functioning in a recipient.

The physiologically compatible, aqueous electrolyte solution of this invention can be varied with only marginal effect on the storage capability of the platelet storage medium. The most desirable embodiments of the platelet storage medium contain the most significant electrolytes found in blood plasma. The electrolytes are contained in the platelet storage medium in the same approximate concentrations as found in normal blood plasma. The most desirable electrolytes include sodium chloride, potassium chloride, calcium chloride, magnesium sulphate, and monobasic sodium phosphate. These and other electrolytes are commonly available in aqueous solutions for injection or infusion into a recipient. In preparing the platelet storage medium the concentration of these electrolytes can be altered by known techniques to obtain an isotonic solution. A desirable embodiment of the platelet storage medium has electrolytes which include, in 1 liter of the medium, between about 6.4 grams and about 7.6 grams of sodium chloride, between about 0.2 gram and about 0.4 gram of potassium chloride, between about 0.1 gram and about 0.4 gram of calcium chloride, between about 0.2 gram and about 0.4 gram of magnesium sulphate, and between about 0.1 gram and about 0.6 gram of monobasic sodium phosphate.

Dextrose is the natural nutrient for blood platelets and significantly contributes to the ability of the platelet storage medium to preserve and maintain viable platelets for extended storage periods beyond a 7 day period. The platelet storage medium of this invention uses dextroses as the only significant nutrient for the stored platelets. An insignificant presence of another nutrient or the use of glucose does not appreciably alter the effectiveness of the platelet storage medium of this invention. The presence of another nutrient is undesirable because other nutrients are not as effective as dextrose in the long term preservation of platelets.

The concentration of dextrose in the platelet storage medium of this invention is higher than the dextrose concentrations typically used in solutions for use with blood or blood components. The higher dextrose concentration must be sufficient to provide nutrients for the stored platelets throughout their storage period. Dextrose is desirably present in the platelet storage medium in a concentration of at least about 3.0 grams per liter. Typically, a concentration of dextrose of between about 3.0 to about 7.5 grams per liter is sufficient to provide platelets, stored according to this invention, with sufficient nutrients for at least about 14 days.

The buffer system of the platelet storage medium of this invention is critical to successful storage of platelets beyond about 5 days. The pH of the platelet concentrates in CPD-plasma drops to levels below 6.0 after about 10 to about 14 days of storage. A pH level below about 6.0 causes the loss of platelet viability and physiological function. The cause for this decrease in platelet viability and function in mediums having a low pH is believed to be due to lactic acid accumulation in the plasma resulting from a continuous and constant rate of glycolysis by the platelets during storage. The addition of a substantial concentration of sodium bicarbonate to the platelet storage medium acts to neutralize the lactic acid formed during platelet storage. The concentration of sodium bicarbonate must be sufficient to maintain a platelet storage medium pH for the stored platelets at above about 6.7 throughout the term of the storage period. A platelet storage medium pH value below about 6.7 can be damaging to the stored platelets as reflected by in vitro parameters such as platelet count, LDH release, ATP levels, hypotonic shock response, the extent of platelet shape change present with ADP, and platelet oxygen consumption rate.

The buffer system of the platelet storage medium of this invention uses sodium bicarbonate as the principal alkaline agent. Sodium bicarbonate is used in concentrations sufficient to maintain the desired pH value of the platelet storage medium throughout platelet storage without precipitation. Desirably, sodium bicarbonate is present in 1 liter of platelet storage medium at a concentration of between about 2.0 grams to about 4.2 grams.

The buffer system of the platelet storage medium of this invention includes monobasic sodium phosphate. Minor concentrations of other salts can be suitable for inclusion with the buffering system of this invention.

The anticoagulant used in the platelet storage medium of this invention includes sodium citrate. In the most preferred embodiments of the invention citric acid is included. The anticoagulants of this invention must be present in concentrations sufficient to prevent substantial coagulation of platelets during extended storage periods. Desirably, sodium citrate is present in 1 liter of platelet storage medium at a concentration of between about 3.0 grams and about 6.0 grams and citric acid is present in 1 liter of platelet storage medium at a concentration of between about 0.4 gram and about 0.6 gram. Minor concentrations of other anticoagulants can be suitable for inclusion in the platelet storage medium of this invention.

The platelet storage medium for blood platelets in accordance with the present invention is composed of the chemical ingredients listed in Table 4. The most desirable embodiments of this invention consist essentially of these compounds to the exclusion of a significant concentration of any other compounds. The exclusion of other compounds in the platelet storage medium of this invention is desirable in order to prevent sensitization in the recipient and to maximize the storage period for platelets.

TABLE 4

| | Concentration Range | Preferred Concentration |
|---|---|---|
| Sodium Chloride | 6.4–7.6 g/l | 6.45 g/l |
| Potassium Chloride | 0.2–0.4 g/l | 0.375 g/l |
| Calcium Chloride | 0.1–0.4 g/l | 0.248 g/l |
| Magnesium Sulfate | 0.2–0.4 g/l | 0.200 g/l |
| Sodium Phosphate (monobasic) | 0.1–0.6 g/l | 0.355 g/l |
| Dextrose | 3.0–7.5 g/l | 7.035 g/l |
| Citric Acid | 0.4–0.6 g/l | 0.510 g/l |
| Tri-Sodium Citrate | 3.0–6.0 g/l | 4.471 g/l |
| Sodium Bicarbonate | 2.0–4.2 g/l | 3.000 g/l |
| $CO_2$ Atmosphere | 2.5–7.5% | 5% |

The individual ionic character of the solution in mE/l is as follows in Table 5:

TABLE 5

| | Range of Ionic Concentration | Preferred Ionic Concentration |
|---|---|---|
| $Na^+$ | 198.8–236.1 | 207.6 |
| $K^+$ | 2.68–5.36 | 5.03 |
| $Ca^{++}$ | 1.36–5.45 | 3.38 |
| $Mg^{++}$ | 1.70–3.40 | 1.70 |
| $HPO_4^{-2}$ | 1.38–5.50 | 2.58 |
| $Cl^-$ | 110.0–138.0 | 117.38 |
| $SO_4^{-2}$ | 1.70–3.40 | 1.70 |
| $HCO_3^-$ | 23.8–50.0 | 35.71 |

The pH of the platelet storage medium is maintained in the range of between about 6.8 and about 7.4.

The basic solutions and ingredients suitable for use in making the platelet storage medium of this invention can be obtained from numerous commercial sources as sterile, non-pyrogenic, injectable solutions. Suppliers for the ingredients can be identified from common publications such as the "Physician's Desk Reference" and the "Red Book" each published by the Medical Economics Company Incorporated, Oradell, N.J. The following examples of commercial ingredients are provided as a sampling of acceptable commercial products available for use in this invention. Ringer's Injection, USP, contains 8.6 grams of sodium chloride, 0.3 gram of potassium chloride, and 0.33 gram of calcium chloride per liter in sterile, non-pyrogenic water for injection. Sterile water for injection is a non-pyrogenic water for intravenous infusion. Magnesium Sulfate Injection, USP, is a 50 percent solution of magnesium sulphate in sterile, non-pyrogenic water for injection. Sodium bicarbonate injection, USP, is an 8.4 percent solution of sodium bicarbonate in sterile, non-pyrogenic water for injection. Dextrose injection solution, USP, is 50 percent solution of dextrose in sterile, non-pyrogenic water for injection. Potassium Chloride Injection, USP, is a 22 percent solution of potassium chloride in sterile, non-pyrogenic water for injection. Anticaoagulant citrate-phosphate-dextrose solution has 3.0 grams of citric acid, 26.3 grams of sodium citrate, 2.22 grams of sodium biphosphate, 25.5 grams of dextrose in one liter sterile, non-pyrogenic water and is used in the proportion of 70 milliliters of CPD to 500 milliliters of whole blood.

In a preferred embodiment, the above listed solutions are combined in the following amounts so as to achieve a chemical consistency for the platelet storage medium of the present invention. The platelet storage medium solution contains 750 milliliters of Ringer's solution, 170 milliliters of CPD, 40 milliliters of sodium bicarbonate solution, 5.4 milliliters of dextrose injection solution, 0.7 milliliter of potassium chloride, 0.4 milliliter of magnesium sulphate solution, and 33.5 milliliters of sterile water for injection. All solutions are combined under sterile, aseptic conditions. Prior to innoculation of platelets with the platelet storage medium, the mixture of the solutions is filter sterilized using a 0.2 micron filter unit designed for the vacuum filtration of tissue culture media.

The preferred composition of the platelet storage medium of the present invention and CPD-plasma are compared in Table 6.

TABLE 6

| | Platelet Storage Medium mEq/l | CPD-Plasma* mEq/l |
|---|---|---|
| Sodium | 207.60 | 173–180 |
| Potassium | 5.03 | 1.9–3.8 |
| Calcium | 3.38 | 3.4–4.0 |
| Magnesium | 1.70 | 1.1–1.9 |
| Phosphate | 2.58 | 3.9 |
| Bicarbonate | 35.71 | 20.9 |
| Citrate | 15.00 | 22.4 |
| Sulphate | 1.70 | 0.4–1.1 |
| Chloride | 117.38 | 75–80 |
| Proteins | 0 | 12.2 |
| Organic Acids | 0 | 4.4 |
| Citric Acid | 2.60 mmol/l | 3.9 mmol/l |
| Dextrose | 40.00 mmol/l | 25.0 mmol/l |

*This concentration assumes that the citrate, citric acid, and phosphate do not enter red cells and is based on a 70 milliliter CPD anticoagulant solution in 500 milliliters of whole blood having a hematocrit of 42.5 and serum chemical values within the normal limits as listed in Harper's Review of Biochemistry.

After the preparation of the platelet storage medium the process for preserving and storing platelets requires the separation of platelets from the other components of blood. A platelet sediment or "button" is obtained after processing a unit of whole blood using conventional blood processing techniques. All the plasma is "expressed off" and collected in a satellite bag. The platelet storage medium can then be transferred into the container holding the platelet sediment. This transfer can be by either connective tubing linking the satellite bag containing the platelet storage medium or commercially available, sterile connection devices that can transfer the medium from a container not originally attached to the collection bag set. After resuspension of the separated platelets in the platelet storage medium, the platelets are stored in a platelet incubator/rotator at about 22° C.

Conventional PL-732 platelet containers have a high permeability to $CO_2$. Storage of the platelets in a 5 percent $CO_2$ atmosphere prevents an initial rise in pH resulting from $CO_2$ escape from the container. This problem can be solved by using a container less permeable to $CO_2$ or by using another non-toxic buffer in combination with sodium bicarbonate.

In order to demonstrate the suitability of the platelet storage medium of the present invention for preserving platelets, in vitro studies were conducted to compare the quality of platelet concentrates stored in the platelet storage medium of the present invention with platelet concentrates stored in plasma anticoagulated with citrate-phosphate-dextrose. The following examples are comparative examples present the results of the comparative tests.

EXAMPLES 1 THROUGH 5 AND COMPARATIVE EXAMPLES A THROUGH E

The procedure used in these examples and comparative examples to separate platelets and to make the platelet storage medium were as described above for the preferred embodiment of the invention. The data presented for the platelet storage medium is designated by the symbol "P.S.M." and represents Examples 1 through 5 for the invention. The data presented for the storage of platelets in CPD-plasma is designated by the symbol "CPD-pl." and represents comparative Examples A through E. The comparative examples do not represent the invention.

For these examples and comparative examples platelets were separated, stored in their respective media, and tested on days 1, 5, 10, and 14. The tests conducted on these days for platelet count determined a percent of the platelet count of the first day, the percent increase in optical density (O.D.) of the extent of platelet shape change with ADP, the percent of hypotonic shock respones, the concentration of adenosine triphosphate or "ATP" in the platelets, and the amount of lysis as evidenced by lactate dehydrogenase or "LDH" released by the platelets. The results of these tests are respectively presented in Tables 7 through 11.

TABLE 7

| | Platelet Count, % of Day 1* | | | |
|---|---|---|---|---|
| | Day 1 | Day 5 | Day 10 | Day 14 |
| P.S.M. | 100 | 94 ± 3 | 91 ± 2 | 82 ± 4 |
| CPD-pl. | 100 | 94 ± 3 | 84 ± 6 | 77 ± 3 |

TABLE 8

| | Extent of Shape Change, % Increase in O.D.* | | | |
|---|---|---|---|---|
| | Day 1 | Day 5 | Day 10 | Day 14 |
| P.S.M. | 16 ± 1 | 14 ± 1 | 10 ± 1 | 7 ± 1 |
| CPD-pl. | 16 ± 1 | 11 ± 1 | 5 ± 1 | 4 ± 1 |

TABLE 9

| | Hypotonic Shock Response, %* | | | |
|---|---|---|---|---|
| | Day 1 | Day 5 | Day 10 | Day 14 |
| P.S.M. | 75 ± 6 | 65 ± 4 | 63 ± 5 | 40 ± 3 |

TABLE 9-continued

| | Hypotonic Shock Response, %* | | | |
|---|---|---|---|---|
| | Day 1 | Day 5 | Day 10 | Day 14 |
| CPD-pl. | 82 ± 3 | 78 ± 5 | 49 ± 2 | 12 ± 5 |

TABLE 10

| | ATP, nmoles/$10^{11}$ plts.* | | | |
|---|---|---|---|---|
| | Day 1 | Day 5 | Day 10 | Day 14 |
| P.S.M. | 8.5 ± 0.4 | 7.7 ± 0.3 | 5.4 ± 0.4 | 3.1 ± 0.4 |
| CPD-pl. | 7.5 ± 0.7 | 6.0 ± 0.4 | 3.5 ± 0.3 | 0.8 ± 0.2 |

TABLE 11

| | LDH, Units Released* | | | |
|---|---|---|---|---|
| | Day 1 | Day 5 | Day 10 | Day 14 |
| P.S.M. | 138 ± 16 | 177 ± 22 | 305 ± 33 | 430 ± 43 |
| CPD-pl. | 120 ± 8 | 215 ± 15 | 430 ± 23 | 585 ± 35 |

*Results represent the mean ± standard deviation.

The results of these comparative studies demonstrate that the platelets stored in the platelet storage medium showed better maintenance of morphologic and physiologic integrity as indicated by the following. The platelets suspended in the platelet storage medium of this invention demonstrated a better preservation as evidenced by the differences in platelet count over the period of testing. A decrease in platelet count reflects platelet clumping and/or lysis. The platelets suspended in the platelet storage medium of this invention demonstrated a better maintenance of the ability of the platelets to undergo shape change or to become activated by using physiologic activators. The platelets suspended in the platelet storage medium of this invention demonstrated a better preservation than the platelets suspended in CPD-plasma by their ability to recover from hypotonic stress. The platelets suspended in the platelet storage medium of this invention demonstrated a better maintenance of the ATP levels which reflects the energy status of the platelet cell. The platelets suspended in the platelet storage medium of this invention demonstrated a better maintenance of membrane integrity as indicated by less loss of intracellular LDH during storage.

These examples and comparative examples demonstrate that storage of platelet concentrates in the platelet storage medium for at least 10 to 14 days at nonfreezing temperatures or a temperature of at least about 22° C. maintain in vitro quality that is reflective of in vivo viability, similar to that obtained with storage of platelets in CPD-plasma for 5 to 10 days.

EXAMPLE 6

Comparative Examples F Through H

This example and comparative examples use the same procedure as described for Examples 1 through 5 and Comparative Examples A through E. This example and comparative examples demonstrate the effect of using various amounts of sodium citrate, sodium chloride, magnesium sulphate, sodium diphosphate, sodium bicarbonate, $pCO_2$ tensions, dextrose, and plasma in different platelet storage media. These modifications were demonstrated by comparing effects of different platelet storage media over a 10 day storage period on (1) platelet count, (2) the percent of hypotonic shock response, (3) the structural integrity of the platelets characterized by change in size distribution, appearance of platelet clumps, balloon forms, fragments as judged by microscopy, and LDH release, (4) platelet function as characterized by the extent of shape change with ADP, and (5) platelet energy metabolism as characterized by the rate of oxygen uptake, lactate production, glucose consumption, and ATP levels. The data demonstrating these characteristics are presented respectively in Tables 12 through 16.

Example 6 presents data for the five characteristics for the platelet storage medium of this invention and is designated by the symbol "P.S.M.". The platelet storage medium used in this example is the preferred embodiment of the invention.

The comparative examples present data for the five characteristics for the platelet storage media designated by the symbols "BSM", "BSM+glucose", and "DMSM". The symbol "BSM" represents a storage medium having the same characteristics of the preferred platelet storage medium of this invention, but does not contain dextrose and has a lower sodium chloride concentration of 5.23 grams per liter. The symbol "BSM+dextrose" represents a storage medium having the same characteristics of the preferred platelet storage medium of this invention, including dextrose, but has the lower sodium chloride concentration of 5.23 grams per liter. The symbol "DMSM" represents a storage medium having the same characteristics of the preferred platelet storage medium, but does not contain dextrose. The comparative examples do not represent the invention.

TABLE 12

| Platelet Count in % of Count at Day 1* | | | |
|---|---|---|---|
| | Day 1 | Day 5 | Day 10 |
| BSM | | 66 ± 8 | 47 ± 11 |
| BSM + dextrose | | 83 ± 8 | 73 ± 10 |
| DMSM | | 82 ± 10 | 56 ± 9 |
| P.S.M. | | 95 ± 2 | 91 ± 3 |

TABLE 13

| Hypotonic Shock Response, % Recovery* | | | |
|---|---|---|---|
| | Day 1 | Day 5 | Day 10 |
| BSM | 28 ± 5 | 20 ± 6 | 4 ± 10 |
| BSM + dextrose | 44 ± 10 | 44 ± 10 | 22 ± 10 |
| DMSM | 75 ± 13 | 41 ± 10 | 8 ± 5 |
| P.S.M. | 73 ± 20 | 61 ± 13 | 51 ± 6 |

TABLE 14

| ADP-Shape Change % Increase in O.D.* | | | |
|---|---|---|---|
| | Day 1 | Day 5 | Day 10 |
| BSM | 13 ± 2 | 7 ± 3 | 2 ± 2 |
| BSM + dextrose | 16 ± 3 | 10 ± 4 | 5 ± 3 |
| DMSM | 15 ± 3 | 8 ± 2 | 1 ± 1 |
| P.S.M. | 17 ± 4 | 14 ± 2 | 10 ± 3 |

TABLE 15

| Rate of Oxygen Consumption nmoles/min/$10^9$ plts* | | | |
|---|---|---|---|
| | Day 1 | Day 5 | Day 10 |
| BSM | 1.0 ± 0.1 | 0.5 ± 0.3 | 0.3 ± 0.1 |
| BSM + dextrose | 1.0 ± 0.3 | 0.6 ± 0.1 | 0.6 ± 0.2 |
| DMSM | 0.9 ± 0.3 | 0.6 ± 0.1 | 0.2 ± 0.1 |
| P.S.M. | 1.0 ± 0.1 | 0.7 ± 0.1 | 0.4 ± 0.3 |

TABLE 16

| ATP, nmoles/$10^9$ plts* | | | |
|---|---|---|---|
| | Day 1 | Day 5 | Day 10 |
| DMSM | 7.1 ± 1.5 | 5.3 ± 2.2 | 0.7 ± 0.2 |
| PSM | 8.5 ± 1.5 | 8.4 ± 1.3 | 6.5 ± 0.8 |

*Results represent mean ± standard deviation.

The results of this example and comparative examples demonstrate the following.

(1) A minimum of 3000 to 6000 milligrams per liter of sodium citrate was essential to avoid platelet clumping and subsequent deterioration of the platelets.

(2) Good maintenance of platelet discoid morphology and negligible clumping was obtained with sodium chloride in the concentration range of 64000 to 76000 milligrams per liter. Poor quality of the platelet concentrate was observed in the data of Table 12 with sodium chloride at a concentration of 5.23 grams per milliliter.

(3) The addition of divalent cations ($Mg^{++}$ and $Ca^{++}$) was necessary for maintenance of platelet discoid morphology. Calcium chloride can be used in the concentration range of 100 to 400 milligrams per liter and magnesium chloride can be used in the range of 200 to 400 milligrams per liter with good results.

(4) Potassium chloride was essential to maintain normal morphology and was used in the concentration range of 220 to 400 milligrams per liter with good results.

(5) Sodium diphosphate was used in the concentration range of 100 to 580 milligrams per liter with good results.

(6) Sodium bicarbonate was used in the the concentration range of 2900 to 4200 milligrams per liter with good results. A minimum of 2900 milligrams per liter was found to be necessary in order to prevent a decrease in pH with storage beyond seven days.

(7) A 2.5 to 7.5 percent carbon dioxide atmosphere, depending on the amount of sodium bicarbonate added, was successfully used to maintain a constant pH.

(8) The addition of glucose (dextrose) was essential for maintenance of good in vitro quality of the platelets as evidenced by the data of Table 12. Dextrose was used in the concentration range of 3000 to 7500 milligrams per liter with good results.

(9) The pH of the platelet storage medium was maintained in the range of 6.8 to 7.4 as measured at 22° C. A pH above 7.4 resulted in clumping of the platelets while a pH below 6.8 caused swelling and loss of discoid morphology.

EXAMPLE 7 AND COMPARATIVE EXAMPLE I

The similarity in chemical and physiological attributes of the platelet storage medium to CPD-plasma are idicative of the inherent non-toxic and safe utility characteristics of the platelet storage medium for infusion into patients. Hence, in vivo study of platelets preserved with the platelet storage medium of this invention was conducted. The studies described herein encompassed 10 paired studies, such as paired studies using normal males over the age of 21 not known to have mental or physical disability and not receiving drug therapy. The volunteers donated one unit of platelet rich plasma which was drawn using the conventional platelet apharesis techniques. This procedure was performed twice. The platelet concentrate was processed for storage for a 7 day period at 22° C. either in CPD-plasma or in the platelet storage medium using currently licensed procedure.

Platelet concentrates were stored in an agitator/incubator at about 22° C. The platelet concentrates in CPD-plasma were stored in an ordinary air atmosphere. The platelet concentrates in the platelet storage medium were stored under a 7.5 percent $CO_2$ atmosphere. This processing and storage of platelet concentrates in CPD plasma is consistent with the currently licensed procedure.

The in vivo viability of the platelets was determined by the conventional percent recovery and survival parameters using radioisotopic labeling techniques well known in the art such as discussed in "Platelet Kinetics and Imaging", Volume I, Techniques and Normal Platelet Kinetics, Heyns et al., CRC Press Inc., Boca Raton, Florida (1985).

At the completion of 7 days of storage, 10 milliliters of platelet concentrate were taken for radioisotopic labeling of the platelets with 111 Indium-Oxine. The washed and labeled platelets were resuspended in 6 milliliters of nonradioactive autologous plasma for infusion into the original donor. Two milliliters of blood samples were drawn from the donors at 1, 2, and 3 hour intervals after infusion and then daily thereafter for 7 days for calculation of in vivo percent recovery and survival. The study was designed such that during the first session 5 donors were infused with platelets stored in the platelet storage medium of this invention and 5 donors were infused with platelets stored in CPD-plasma. This was repeated during the second session, 2 months later, with the storage medium being reversed for the donors. The percent recoveries and survivals were determined using the gamma function multiple hit program. Paired t-tests were used to detect significant differences. The in vitro viability of the platelets was evaluated by hypotonic shock response and extent of shape change with ADP. The results of the percent of in vivo recovery and survivals are shown in Tables 17 and 18, respectively.

TABLE 17

| | IN VIVO Recovery %, % | |
|---|---|---|
| Donor | CPD-plasma | P.S.M. |
| 1 | 29 | 57 |
| 2 | 23 | 52 |
| 3 | 36 | 52 |
| 4 | 43 | 47 |
| 5 | 31 | 52 |
| 6 | 61 | 66 |
| 7 | 33 | 48 |
| 8 | 28 | 37 |
| 9 | 41 | 44 |
| 10 | 43 | 55 |
| mean ± standard deviation | 37 ± 11 | 51 ± 8 |

TABLE 18

| | Survivals, Hours | |
|---|---|---|
| Donor | CPD-plasma | P.S.M. |
| 1 | 54 | 125 |
| 2 | 85 | 162 |
| 3 | 126 | 159 |
| 4 | 171 | 145 |
| 5 | 103 | 155 |
| 6 | 86 | 146 |
| 7 | 122 | 150 |
| 8 | 107 | 114 |
| 9 | 129 | 154 |
| 10 | 121 | 130 |
| mean ± standard deviation | 110 ± 32 | 144 ± 16 |

Mean percent in vivo recoveries and survivals were found to be substantially higher with platelet concentrates stored in platelet storage medium or 51±8 percent and 144±16 hours versus 37±11 percent and 110±32 hours for platelet concentrate stored in CPD-plasma, respectively. The differences were statistically, highly significant as witnessed by a t-test value of $P<0.005$. The in vitro viability results paralleled the in vitro results as evidenced by the data presented in Tables 19 and 20 with statistically superior results indicated by the paired t-test value of $p<0.01$ for platelet concentrates stored in platelet storage medium.

TABLE 19

| | Hypotonic Shock Response, % Recovery | |
|---|---|---|
| Donor | CPD-plasma | P.S.M. |
| 1 | 18 | 75 |
| 2 | 39 | 57 |
| 3 | 47 | 62 |
| 4 | 40 | 60 |
| 5 | 35 | 58 |
| 6 | 44 | 70 |
| 7 | 47 | 67 |
| 8 | 40 | 50 |
| 9 | 50 | 55 |
| 10 | 77 | 100 |
| mean ± standard deviation | 44 ± 15 | 65 ± 14 |

TABLE 20

| | Extent of Shape Change with ADP | |
|---|---|---|
| Donor | CPD-plasma | P.S.M. |
| 1 | 4 | 12 |
| 2 | 6 | 13 |
| 3 | 8 | 19 |
| 4 | 7 | 14 |
| 5 | 10 | 13 |
| 6 | 8 | 14 |
| 7 | 17 | 18 |
| 8 | 7 | 11 |
| 9 | 14 | 11 |
| 10 | 19 | 17 |
| mean ± standard deviation | 9 ± 4 | 14 ± 3 |

The results of this example and comparative example indicate that the in vivo viability of platelet concentrates are substantially improved in the platelet storage medium of this invention when compared to platelet storage in CPD-plasma.

In the claims:

1. A sterile, plasma-free platelet storage medium comprising:
   a physiologically compatible, aqueous electrolyte solution, one liter of said electrolyte solution having:
   between about 3.0 grams and about 7.5 grams of dextrose;
   between about 3.0 grams and about 6.0 grams of sodium citrate; and between about 2.0 grams and about 4.2 grams of sodium bicarbonate;

said platelet storage medium being isotonic and having a pH in a range of between about 6.8 and about 7.4, said platelet storage medium being capable of preserving platelets for at least about 10 days at a temperature of at least about 22° C.

2. The platelet storage medium according to claim 1 further comprising citric acid, said citric acid being in a concentration of 1 liter of said platelet storage medium of about 0.51 gram and said dextrose being in a concentration of about 7.035 grams, said sodium citrate being in a concentration of about 4.471 grams, and said sodium bicarbonate being in a concentration of about 3.0 grams.

3. The platelet storage medium according to claim 1 wherein one liter of said electrolyte solution has electrolytes including:
between about 6.4 grams and about 7.6 grams of sodium chloride;
between about 0.2 gram and about 0.4 gram of potassium chloride;
between about 0.1 gram and about 0.4 gram of calcium chloride;
between about 0.2 gram and about 0.4 gram of magnesium sulphate; and
between about 0.1 gram and about 0.6 gram of monobasic sodium phosphate.

4. The platelet storage medium according to claim 3 wherein said electrolytes include:
about 6.45 grams of sodium chloride;
about 0.375 gram of potassium chloride;
about 0.248 gram of calcium chloride;
about 0.2 gram of magnesium sulphate; and
about 0.355 gram of monobasic sodium phosphate.

5. The platelet storage medium according to claim 4 further comprising citric acid, said citric acid being in a concentration of 1 liter of said platelet storage medium of about 0.51 gram and said dextrose being in a concentration of about 7.035 grams, said sodium citrate being in a concentration of about 4.471 grams, and said sodium bicarbonate being in a concentration of about 3.0 grams.

6. The platelet storage medium according to claim 5 further comprising a human blood platelet concentrate.

7. A sterile, plasma-free platelet storage medium consisting essentially of:
a physiologically compatible, aqueous electrolyte solution, one liter of said electrolyte solution having:
between about 3.0 grams and about 7.5 grams of dextrose;
between about 3.0 grams and about 6.0 grams of sodium citrate; and
between about 0.4 gram and about 0.6 gram of citric acid;
between about 2.0 grams and about 4.2 grams of sodium bicarbonate;
said platelet storage medium being isotonic and having a pH in a range of between about 6.8 and about 7.4, whereby said platelet storage medium preserves platelets for at least about 14 days at a temperature of at least about 22° C.

8. The platelet storage medium according to claim 7 wherein said dextrose is in a concentration of about 7.035 grams, said sodium citrate is in a concentration of about 4.471 grams, said citric acid is in a concentration of about 0.51 gram, and said sodium bicarbonate is in a concentration of about 3.0 grams.

9. The platelet storage medium according to claim 7 wherein one liter of said electrolyte solution has electrolytes including:
between about 6.4 grams and about 7.6 grams of sodium chloride;
between about 0.2 gram and about 0.4 gram of potassium chloride;
between about 0.1 gram and about 0.4 gram of calcium chloride;
between about 0.2 gram and about 0.4 gram of magnesium sulphate; and
between about 0.1 gram and about 0.6 gram of monobasic sodium phosphate.

10. The platelet storage medium according to claim 9 wherein said electrolytes include:
about 6.45 grams of sodium chloride;
about 0.375 gram of potassium chloride;
about 0.248 gram of calcium chloride;
about 0.2 gram of magnesium sulphate; and
about 0.355 gram of monobasic sodium phosphate.

11. The platelet storage medium according to claim 10 wherein said dextrose is in a concentration of about 7.035 grams, said sodium citrate is in a concentration of about 4.471 grams, said citric acid is in a concentration of about 0.51 gram, and said sodium bicarbonate is in a concentration of about 3.0 grams.

12. A sterile, plasma-free platelet storage medium consisting essentially of:
distilled water, one liter of said distilled water having:
between about 6.4 grams and about 7.6 grams of sodium chloride;
between about 0.2 gram and about 0.4 gram of potassium chloride;
between about 0.1 gram and about 0.4 gram of calcium chloride;
between about 0.2 gram and about 0.4 gram of magnesium sulphate;
between about 0.1 gram and about 0.6 gram of monobasic sodium phosphate;
between about 3.0 grams and about 7.5 grams of dextrose;
between about 3.0 grams and about 6.0 grams of sodium citrate; and
between about 2.0 grams and about 4.2 grams of sodium bicarbonate;
said platelet storage medium being isotonic and having a pH in a range of between about 6.8 and about 7.4.

13. The platelet storage medium according to claim 12 wherein said dextrose is in a concentration of about 7.035 grams, said sodium citrate is in a concentration of about 4.471 grams, said citric acid is in a concentration of about 0.51 gram, and said sodium bicarbonate is in a concentration of about 3.0 grams.

14. The platelet storage medium according to claim 13 wherein said electrolytes are in concentrations of:
about 6.45 grams of sodium chloride;
about 0.375 gram of potassium chloride;
about 0.248 gram of calcium chloride;
about 0.2 gram of magnesium sulphate; and
about 0.355 gram of monobasic sodium phosphate.

15. A process for preserving platelets in a sterile, plasma-free platelet storage medium comprising:
preparing a physiologically compatible, aqueous electrolyte solution, one liter of said electrolyte solution having:

between about 3.0 grams and about 7.5 grams of dextrose;

between about 3.0 grams and about 6.0 grams of sodium citrate; and between about 2.0 grams and about 4.2 grams of sodium bicarbonate;

suspending platelets in said platelet storage medium, said platelet storage medium being isotonic and having a pH in a range of between about 6.8 and about 7.4, whereby a substantial concentration of said platelets remain viable for at least about 14 days at a temperature of at least about 22° C.

16. The process for preserving platelets according to claim 15 wherein said platelet storage medium includes citric acid, said citric acid being in a concentration of 1 liter of said platelet storage medium of about 0.51 gram and said dextrose is in a concentration of about 7.035 grams, said sodium citrate is in a concentration of about 4.471 grams, and said sodium bicarbonate is in a concentration of about 3.0 grams.

17. The process for preserving platelets according to claim 16 wherein one liter of said electrolyte solution has electrolytes including:

between about 6.4 grams and about 7.6 grams of sodium chloride;

between about 0.2 gram and about 0.4 gram of potassium chloride;

between about 0.1 gram and about 0.4 gram of calcium chloride;

between about 0.2 gram and about 0.4 gram of magnesium sulphate; and between about 0.1 gram and about 0.6 gram of monobasic sodium phosphate.

18. The process for preserving platelets according to claim 17 wherein said electrolytes include:

about 6.45 grams of sodium chloride;

about 0.375 gram of potassium chloride;

about 0.248 gram of calcium chloride;

about 0.2 gram of magnesium sulphate; and about 0.355 gram of monobasic sodium phosphate.

19. A product of the process according to claim 15.

20. A product of the process according to claim 18.

* * * * *